(12) United States Patent
Lydecker et al.

(10) Patent No.: US 12,285,539 B2
(45) Date of Patent: Apr. 29, 2025

(54) HEMOSTATIC COMPOSITIONS AND RELATED METHODS

(71) Applicant: Boston Scientific Scimed, Inc., Maple Grove, MN (US)

(72) Inventors: Lauren Lydecker, Millbury, MA (US); Poorva Rajguru, Shoreview, MN (US); David Wulfman, Minneapolis, MN (US); Joseph Rausa, Littleton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

(21) Appl. No.: 17/233,101

(22) Filed: Apr. 16, 2021

(65) Prior Publication Data

US 2021/0322629 A1 Oct. 21, 2021

Related U.S. Application Data

(60) Provisional application No. 63/011,492, filed on Apr. 17, 2020.

(51) Int. Cl.
*A61L 26/00* (2006.01)
*C08K 3/011* (2018.01)
*C08K 3/32* (2006.01)
*C08L 5/08* (2006.01)

(52) U.S. Cl.
CPC ....... *A61L 26/0023* (2013.01); *A61L 26/0076* (2013.01); *A61L 26/0085* (2013.01); *C08K 3/011* (2018.01); *C08K 3/32* (2013.01); *C08L 5/08* (2013.01); *A61L 2400/04* (2013.01); *C08K 2003/324* (2013.01)

(58) Field of Classification Search
CPC ............ A61L 26/0023; A61L 26/0076; A61L 26/0085; A61L 2400/04; A61L 24/0026; A61L 24/0036; A61L 24/08; A61L 24/001; A61L 2400/06; C08K 3/011; C08K 3/32; C08K 2003/324; C08K 5/521; C08L 5/08; C08J 3/122
See application file for complete search history.

(56) References Cited

U.S. PATENT DOCUMENTS

| | | |
|---|---|---|
| 471,854 A | 3/1892 | Howard |
| 881,238 A | 3/1908 | Hasbrouck |
| 1,145,520 A | 7/1915 | Smith |
| 1,599,959 A | 9/1926 | Buheiji |
| 1,732,566 A | 10/1929 | McKendrick |
| 2,151,418 A | 3/1939 | Bolté |
| 2,185,927 A | 6/1940 | Shelanski |
| 2,478,715 A | 8/1949 | Schmitt |
| 2,623,519 A | 12/1952 | Cohen |
| 3,669,113 A | 6/1972 | Altounyan et al. |
| 3,940,061 A | 2/1976 | Gimple et al. |
| 4,184,258 A | 6/1980 | Barrington et al. |
| 4,427,450 A | 1/1984 | Kostansek |
| 4,457,329 A | 7/1984 | Werley et al. |
| 4,806,167 A | 2/1989 | Raythatha |
| 5,215,221 A | 6/1993 | Dirksing |
| 5,231,983 A | 8/1993 | Matson et al. |
| 5,273,531 A | 12/1993 | Knoepfler |
| 5,312,331 A | 5/1994 | Knoepfler |
| 5,312,333 A | 5/1994 | Churinetz et al. |
| 5,366,122 A | 11/1994 | Guentert et al. |
| 5,445,612 A | 8/1995 | Terakura et al. |
| 5,470,311 A | 11/1995 | Setterstrom et al. |
| 5,884,621 A | 3/1999 | Matsugi et al. |
| 5,951,531 A | 9/1999 | Ferdman et al. |
| 6,003,512 A | 12/1999 | Gerde |
| 6,060,461 A * | 5/2000 | Drake .................... A61L 24/08 514/60 |
| 6,484,750 B1 | 11/2002 | Foos et al. |
| 6,554,022 B2 | 4/2003 | Wakeman |
| 6,589,087 B2 | 7/2003 | Mackal et al. |
| 6,684,917 B2 | 2/2004 | Zhu et al. |
| 6,708,712 B2 | 3/2004 | Wakeman |

(Continued)

FOREIGN PATENT DOCUMENTS

| | | |
|---|---|---|
| CN | 102172498 A | 9/2011 |
| CN | 101401956 B | 11/2012 |

(Continued)

OTHER PUBLICATIONS

Biranje, Santosh S., et al. "Hemostasis and anti-necrotic activity of wound-healing dressing containing chitosan nanoparticles." International journal of biological macromolecules 121 (2019): 936-946. (Year: 2019).*
Maeng et al. Journal of Biomedical Materials Research Part A: An Official Journal of The Society for Biomaterials, The Japanese Society for Biomaterials, and The Australian Society for Biomaterials and the Korean Society for Biomaterials 92.3 (2010): 869-876. (Year: 2010).*
Xu et al. (Journal of microencapsulation 24.2 (2007): 143-151. (Year: 2007).*
Abyadeh, Morteza, et al. Avicenna journal of medical biotechnology 9.3 (2017): 126. (Year: 2017).*
Xiong et al. Journal of Microencapsulation 24.2 (2007): 143-151. (Year: 2007).*

(Continued)

*Primary Examiner* — Mina Haghighatian
*Assistant Examiner* — Janice Y Silverman
(74) *Attorney, Agent, or Firm* — Bookoff McAndrews, PLLC (57) ABSTRACT

Compositions including a plurality of particles that may be prepared from a chitosan salt and methods for preparing the same. The plurality of particles may have an average diameter ranging from about 100 μm to about 750 μm, such as from about 150 μm to about 500 μm; a steepness value ranging from about 30 to about 90; and an average aspect ratio greater than 0.6. The plurality of particles may be substantially spherical in shape, for example. Methods of preparation include electrospraying a chitosan salt solution through a needle.

12 Claims, 6 Drawing Sheets

(56) References Cited

U.S. PATENT DOCUMENTS

| | | |
|---|---|---|
| 6,716,190 B1 | 4/2004 | Glines et al. |
| 6,799,571 B1 | 10/2004 | Hughes et al. |
| 7,178,547 B2 | 2/2007 | Mackal |
| 7,311,270 B2 | 12/2007 | Kapila |
| 7,334,598 B1 | 2/2008 | Hollars |
| 7,361,300 B2 | 4/2008 | Kelly et al. |
| 7,427,607 B2 | 9/2008 | Suzuki |
| 7,455,248 B2 | 11/2008 | Kablik et al. |
| 7,461,649 B2 | 12/2008 | Gamard et al. |
| 7,544,177 B2 | 6/2009 | Gertner |
| 7,563,299 B2 | 7/2009 | Baptista da Costa et al. |
| 7,673,647 B2 | 3/2010 | Mackal |
| 7,841,338 B2 | 11/2010 | Dunne et al. |
| 7,892,205 B2 | 2/2011 | Palasis et al. |
| 7,921,874 B2 | 4/2011 | Tekulve et al. |
| 8,037,880 B2 | 10/2011 | Zhu et al. |
| 8,097,071 B2 | 1/2012 | Burgess et al. |
| 8,118,777 B2 | 2/2012 | Ducharme et al. |
| 8,269,058 B2 | 9/2012 | McCarthy et al. |
| 8,313,474 B2 | 11/2012 | Campbell et al. |
| 8,360,276 B2 | 1/2013 | Rogier et al. |
| 8,361,054 B2 | 1/2013 | Ducharme et al. |
| 8,496,189 B2 | 7/2013 | Lomond et al. |
| 8,673,065 B2 | 3/2014 | Burgess et al. |
| 8,721,582 B2 | 5/2014 | Ji |
| 8,728,032 B2 | 5/2014 | Ducharme et al. |
| 8,741,335 B2 | 6/2014 | McCarthy |
| 8,827,980 B2 | 9/2014 | Ji |
| 8,910,627 B2 | 12/2014 | Iwatschenko et al. |
| 8,951,565 B2 | 2/2015 | McCarthy |
| 9,028,437 B2 | 5/2015 | Ott et al. |
| 9,089,658 B2 | 7/2015 | Dunne et al. |
| 9,101,744 B2 | 8/2015 | Ducharme |
| 9,107,668 B2 | 8/2015 | Melsheimer et al. |
| 9,132,206 B2 | 9/2015 | McCarthy |
| 9,204,957 B2 | 12/2015 | Gregory et al. |
| 9,205,170 B2 | 12/2015 | Lucchesi et al. |
| 9,205,207 B2 | 12/2015 | Ji |
| 9,205,240 B2 | 12/2015 | Greenhalgh et al. |
| 9,308,584 B2 | 4/2016 | Burgess et al. |
| 9,310,812 B2 | 4/2016 | Costle et al. |
| 9,375,533 B2 | 6/2016 | Ducharme et al. |
| 9,492,646 B2 | 11/2016 | Hoogenakker et al. |
| 9,517,976 B2 | 12/2016 | Mackal |
| 9,545,490 B2 | 1/2017 | Iwatschenko et al. |
| 9,555,185 B2 | 1/2017 | Foster et al. |
| 9,629,966 B2 | 4/2017 | Ji |
| 9,636,470 B2 | 5/2017 | Pohlmann et al. |
| 9,707,359 B2 | 7/2017 | Kubo |
| 9,713,682 B2 | 7/2017 | Eistetter et al. |
| 9,717,897 B2 | 8/2017 | Rogier |
| 9,821,084 B2 | 11/2017 | Diegelmann et al. |
| 9,839,772 B2 | 12/2017 | Ducharme |
| 9,839,774 B2 | 12/2017 | Bonaldo |
| 9,846,439 B2 | 12/2017 | Carman et al. |
| 9,867,931 B2 | 1/2018 | Gittard |
| 9,976,660 B2 | 5/2018 | Stanton et al. |
| 10,004,690 B2 | 6/2018 | Lee et al. |
| 10,010,705 B2 | 7/2018 | Greenhalgh et al. |
| 10,017,231 B2 | 7/2018 | Fawcett, Jr. |
| 10,036,617 B2 | 7/2018 | Mackal |
| 10,065,004 B2 | 9/2018 | Eder et al. |
| 10,173,019 B2 | 1/2019 | Kaufmann et al. |
| 10,384,049 B2 | 8/2019 | Stanton et al. |
| 10,463,811 B2 | 11/2019 | Lee et al. |
| 10,507,293 B2 | 12/2019 | Goodman et al. |
| 10,646,706 B2 | 5/2020 | Rogier |
| 10,730,595 B2 | 8/2020 | Fawcett |
| 10,751,523 B2 | 8/2020 | Rogier |
| 10,806,853 B2 | 10/2020 | Gittard |
| 10,850,814 B2 | 12/2020 | Fawcett |
| 10,994,818 B2 | 5/2021 | Hernandez |
| 2004/0107963 A1 | 6/2004 | Finlay et al. |
| 2004/0249359 A1 | 12/2004 | Palasis et al. |
| 2005/0121025 A1 | 6/2005 | Gamard et al. |
| 2005/0147656 A1 | 7/2005 | McCarthy et al. |
| 2005/0220721 A1 | 10/2005 | Kablik et al. |
| 2006/0004314 A1 | 1/2006 | McCarthy et al. |
| 2006/0213514 A1 | 9/2006 | Price et al. |
| 2007/0056586 A1 | 3/2007 | Price et al. |
| 2007/0066920 A1 | 3/2007 | Hopman et al. |
| 2007/0066924 A1 | 3/2007 | Hopman et al. |
| 2007/0082023 A1 | 4/2007 | Hopman et al. |
| 2007/0125375 A1 | 6/2007 | Finlay et al. |
| 2007/0151560 A1 | 7/2007 | Price et al. |
| 2007/0083137 A1 | 8/2007 | Hopman et al. |
| 2007/0199824 A1 | 8/2007 | Hoerr et al. |
| 2008/0021374 A1 | 1/2008 | Kawata |
| 2008/0287907 A1 | 11/2008 | Gregory et al. |
| 2009/0101144 A1 | 4/2009 | Gamard et al. |
| 2009/0155342 A1 | 6/2009 | Diegemann et al. |
| 2009/0281486 A1 | 11/2009 | Ducharme |
| 2010/0121261 A1 | 5/2010 | Kablik et al. |
| 2010/0172958 A1* | 7/2010 | Lucchesi .................. A61L 15/28 424/445 |
| 2010/0305505 A1 | 12/2010 | Ducharme et al. |
| 2011/0073200 A1 | 3/2011 | Overvaag et al. |
| 2011/0274726 A1 | 11/2011 | Guo et al. |
| 2011/0308516 A1 | 12/2011 | Price et al. |
| 2013/0316974 A1* | 11/2013 | Wang .................. A61L 26/0023 536/57 |
| 2014/0271491 A1 | 9/2014 | Gittard et al. |
| 2015/0094649 A1 | 4/2015 | Gittard |
| 2015/0125513 A1 | 5/2015 | McCarthy |
| 2016/0375202 A1 | 12/2016 | Goodman et al. |
| 2017/0035929 A1 | 2/2017 | Phillips et al. |
| 2017/0106181 A1 | 4/2017 | Bonaldo et al. |
| 2017/0232141 A1 | 8/2017 | Surti et al. |
| 2017/0252479 A1 | 9/2017 | Ji et al. |
| 2017/0296760 A1 | 10/2017 | Lee et al. |
| 2017/0326275 A1 | 11/2017 | Lecler et al. |
| 2018/0000737 A1 | 1/2018 | Bertonis et al. |
| 2018/0099088 A1 | 4/2018 | Gittard |
| 2018/0193574 A1 | 7/2018 | Smith et al. |
| 2018/0214160 A1 | 8/2018 | Hoskins et al. |
| 2018/0339144 A1 | 11/2018 | Greenhalgh et al. |
| 2019/0134366 A1 | 5/2019 | Erez et al. |
| 2019/0217315 A1 | 7/2019 | Maguire et al. |
| 2019/0232030 A1 | 8/2019 | Pic et al. |
| 2021/0024187 A1 | 1/2021 | Fawcett et al. |
| 2021/0069485 A1 | 3/2021 | Rogier |

FOREIGN PATENT DOCUMENTS

| | | |
|---|---|---|
| CN | 105903064 A | 8/2016 |
| DE | 60215438 T2 | 8/2007 |
| EP | 3052168 B1 | 11/2019 |
| JP | H07118305 A | 5/1995 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2008033462 A2 | 3/2008 |
| WO | 2009061409 A1 | 5/2009 |
| WO | 2015050814 A1 | 4/2015 |
| WO | WO-2018049310 A1 * | 3/2018 ............ C01F 11/185 |
| WO | 2018157772 A1 | 9/2018 |

OTHER PUBLICATIONS

Darwin Microfluidics downloaded on Jan. 11, 2023 from URL:<https://darwin-microfluidics.com/blogs/tools/syringe-needle-gauge-table> 2019. (Year: 2019).*
Chen et al. J. Mater. Chem. B, 2017, 5, 3686-3696. (Year: 2017).*
Tapia-Hernandez et al. J. Agric. Food Chem. 2015, 63, 4699-4707. (Year: 2015).*
Sonnekus, Jolanda. Characterization of the flow and compression properties of chitosan. Diss. North-West University, 2008. (Year: 2008).*
Songsurang et al. Arch Pharm Res vol. 34, No. 4, 583-592, 2011. (Year: 2011).*

(56) References Cited

OTHER PUBLICATIONS

Kim et al. Carbohydrate Polymers 84 (2011) 1329-1336. (Year: 2011).*
Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.
Giday, Samuel, et al. "Safety analysis of a hemostatic powder in a porcine model of acute severe gastric bleeding." Digestive diseases and sciences 58.12 (2013): 3422-3428.
Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.
Regalia, Kristen, et al. "Hemospray in Gastrointestinal Bleeding." Practical Gastroenterology. Endoscopy: Opening New Eyes, ser. 8, May 2014, pp. 13-24. 8.
Cook Medical. Hemospray Endoscopic Hemostat, COOK, 2014. (7 pages, in English).
"Hemospray Clinical Experience Shows Efficacy of a New Hemostasis Modality—v1", Cook Medical, 2012.
"Hemospray Clinical Experience Shows Efficacy of a New Hemostasis Modality—v2", Cook Medical, 2013.
"Hemospray Clinical Experience Shows Efficacy of a New Hemostasis Modality—v3", Cook Medical, 2014.
Aslanian, Harry R., and Loren Laine. "Hemostatic powder spray for GI bleeding." Gastrointestinal endoscopy 77.3 (2013): 508-510.
Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.
Retsch GmbH Haan. Sieve Analysis: Taking a Close Look at Quality, An Expert Guide to Particle Size Analysis. 2015. (56 pages, in English).
Micromeritics. Density Analysis, 2001. (6 pages, in English).
Micromeritics. "Application Note: Bulk and Skeletal Density Computations for the AutoPore." May 2012. (3 pages, in English).
Arefnia, Ali, et al. "Comparative Study on the Effect of Tire-Derived Aggregate on Specific Gravity of Kaolin." Electronic Journal of Geotechnical Engineering 18 (2013): 335-44.
Kesavan, Jana, et al. "Density Measurements of Materials Used in Aerosol Studies". Edgewood Chemical Biological Center Aberdeen Proving Ground MD, 2000.
Donghong, L et al., "Enhanced Hemostatic Performance Of Tranexamic Acid-Loaded Chitosan/Alginate Composite Microparticles," *J. Biomed. Biotech.*, vol. 2012, pp. 1-9 (Jan. 1, 2012).
Helbling, I.M et al., "Preparation Of TPP-Crosslinked Chitosan Microparticles By Spray Drying For The Controlled Delivery Of Progesterone Intended For Estrus Synchronization In Cattle," *Pharmaceutical Research*, vol. 35, No. 3, pp. 1-15 (Feb. 20, 2018).
Kumbar, S.G. et al., "Crosslinked Chitosan Microspheres For Encapsulation Of Diclofenac Sodium: Effect Of Crosslinking Agent," *J. Microencapsulation*, vol. 19, No. 2, pp. 173-180 (Jan. 29, 2002).
Phromosopha, T. et al., "Chitosan Microparticles Prepared By The Water-In-Oil Emulsion Solvent Diffusion Method For Drug Delivery," *Biotechnology*, pp. 61-66 (Jan. 1, 2010).
International Search Report in PCT/US2021/027753, dated Jul. 8, 2021 (6 pages).
Office Action in Chinese Application No. 202180042885.X, dated Feb. 21, 2024 (9 pages).
Communication in European Application No. 21723602.5, dated Feb. 27, 2025 (6 pages).

* cited by examiner

HEMOSTATIC COMPOSITIONS AND RELATED METHODS

CROSS-REFERENCE TO RELATED APPLICATIONS

This application claims the benefit of priority from U.S. Provisional Application No. 63/011,492, filed Apr. 17, 2020, which is incorporated by reference herein in its entirety.

TECHNICAL FIELD

The present disclosure relates generally to therapeutic materials and related methods of preparation and treatment. More specifically, the present disclosure includes hemostatic materials for treating tissue.

BACKGROUND

Hemostatic agents are used to treat bleeding of internal and external wounds in efforts to prevent numerous medical concerns, including blood loss and infection. To treat internal wounds, e.g., gastrointestinal hemorrhages, hemostatic agents may be applied via suitable medical devices. However, delivery of such agents to a target site inside the body can present challenges.

SUMMARY OF THE DISCLOSURE

The present disclosure includes therapeutic materials and methods of preparation and treatment thereof. For example, the present disclosure includes a composition comprising a plurality of particles that may be prepared from a polysaccharide salt, e.g., a chitosan salt. Thus, for example, the plurality of particles may comprise chitosan. The chitosan of the particles may comprise or be the form of chitosan with a crosslinking agent (e.g., a crosslinking agent for chitosan) and/or a chitosan salt, for example. According to some aspects, the plurality of particles may comprise chitosan and a crosslinking agent, wherein the plurality of particles may be prepared from a chitosan salt. The plurality of particles may have an average diameter (average CE diameter) ranging from about 100 μm to about 1 mm, such as from about 100 μm to about 750 μm, from about 150 μm to about 500 μm, from about 250 μm to about 900 μm, from about 250 μm to about 500 μm, from about 400 μm to about 600 μm, from about 550 μm to about 750 μm, or from about 300 μm to about 450 μm. The plurality of particles may have a steepness value ranging from about 30 to about 90, such as from about 50 to about 80, from about 70 to about 90, or from about 60 to about 80. Additionally or alternatively, the plurality of particles may have an average aspect ratio greater than 0.6, greater than 0.7, or greater than 0.8. For example, the plurality of particles may be substantially spherical in shape. An average of a maximum distance of the plurality of particles may range from about 500 μm to about 700 μm, for example.

According to some aspects of the present disclosure, the plurality of particles may have an average diameter ranging from about 150 μm to about 500 μm and an average aspect ratio greater than 0.6, and optionally a steepness value ranging from about 30 to about 90. For example, the plurality of particles may have an average diameter ranging from about 150 μm to about 500 μm and an average aspect ratio greater than 0.7, and optionally a steepness value ranging from about 50 to about 80. Further, for example, the plurality of particles may have an average diameter ranging from about 150 μm to about 500 μm and an average aspect ratio greater than 0.6, and optionally a steepness value ranging from about 60 to about 80. In at least one example, the plurality of particles has an average diameter ranging from about 300 μm to about 450 μm and an average aspect ratio greater than 0.6, and optionally a steepness value ranging from about 30 to about 90. Further, for example, the plurality of particles may have an average diameter ranging from about 300 μm to about 450 μm and an average aspect ratio greater than 0.7, and optionally a steepness value ranging from about 30 to about 90. In at least one example, the plurality of particles has an average diameter ranging from about 300 μm to about 450 μm and an average aspect ratio greater than 0.7, and optionally a steepness value ranging from about 50 to about 80. Further, for example, the plurality of particles may have an average diameter ranging from about 300 μm to about 450 μm and an average aspect ratio greater than 0.8, and optionally a steepness value ranging from about 30 to about 90.

A bulk density of the plurality of particles may range from about 0.05 g/mL to about 0.7 g/mL, such as about 0.1 g/mL to about 0.7 g/mL, about 0.2 g/mL to about 0.7 g/mL, about 0.05 g/mL to about 0.4 g/mL, about 0.3 g/mL to about 0.5 g/mL, or about 0.1 g/mL to about 0.2 g/mL. For example, the plurality of particles may have an average diameter ranging from about 150 μm to about 500 μm and an average aspect ratio greater than 0.6, optionally a steepness value ranging from about 30 to about 90, and a bulk density ranging from about 0.1 g/mL to about 0.7 g/mL. Further, for example, the plurality of particles may have an average diameter ranging from about 150 μm to about 500 μm and an average aspect ratio greater than 0.7, optionally a steepness value ranging from about 30 to about 90, and a bulk density ranging from about 0.3 g/mL to about 0.5 g/mL. The plurality of particles may have a porosity greater than 80%, as measured by mercury intrusion porosimetry, such as a porosity ranging from about 85% to about 95%. In some examples herein, the plurality of particles has an average diameter ranging from about 150 μm to about 500 μm, an average aspect ratio greater than 0.6, and optionally a steepness value ranging from about 30 to about 90, a bulk density ranging from about 0.1 g/mL to about 0.7 g/mL, and a porosity greater than 80%, as measured by mercury intrusion porosimetry. For example, the plurality of particles may have an average diameter ranging from about 150 μm to about 500 μm, an average aspect ratio greater than 0.7, and optionally a steepness value ranging from about 30 to about 90, a bulk density ranging from about 0.1 g/mL to about 0.7 g/mL, and a porosity ranging from about 85% to about 95%, as measured by mercury intrusion porosimetry.

In some examples, the chitosan salt that can be used to prepare the particles is chitosan acetate, chitosan lactate, chitosan succinate, chitosan glutamate, chitosan glycolate, or chitosan citrate. The compositions herein may comprise a plurality of particles comprising chitosan and a crosslinking agent, optionally wherein the crosslinking agent comprises tripolyphosphate, e.g., sodium tripolyphosphate. Additionally, the composition may further comprise a fluid, such as a liquid. Additionally, or alternatively, the composition may be in the form of a powder.

Also disclosed therein are uses of a composition as a hemostatic agent, wherein the composition may be a composition as described above and/or elsewhere herein.

The present disclosure also includes methods of preparing a composition as described above and/or elsewhere herein, the method comprising electrospraying a chitosan salt solution through a needle. Electrospraying the chitosan salt solution through a needle may produce a plurality of particles that comprise chitosan. For example, electrospraying the chitosan salt solution through a needle and into an aqueous solution comprising a crosslinking agent may produce a plurality of particles that comprise chitosan and the crosslinking agent. The chitosan salt solution used to prepare the particles may have a viscosity at 25° C. ranging from about 1,500 cPs to about 8,000 cPs, e.g., from about 1,500 cPs to about 3,000 cPs, and additionally, or alternatively, may comprise from about 0.5% to about 10% by weight chitosan relative to the volume of the solution. The electrospraying may include applying a voltage of about 9 kV to about 25 kV or about 10 kV to about 30 kV to the needle. The needle may be a 21 gauge needle, a 22 gauge needle, or a 23 gauge needle, for example. The method may include electrospraying the chitosan salt solution into an aqueous solution comprising a crosslinking agent such as sodium tripolyphosphate; freeze drying the plurality of particles, wherein the freeze drying may be performed for a period of time ranging from 30 minutes to 48 hours, such as from 2 hours to 12 hours, or 4 hours to 6 hours; and rinsing the plurality of particles with a liquid after electrospraying and/or before freeze drying. In the some examples, the liquid may comprise water, an alcohol, or a mixture thereof.

BRIEF DESCRIPTION OF THE FIGURES

The accompanying drawings, which are incorporated in and constitute a part of this specification, illustrate various exemplary embodiments and together with the description, serve to explain the principles of the disclosed embodiments.

DETAILED DESCRIPTION

Particular aspects of the present disclosure are described in greater detail below. The terms and definitions provided herein control, if in conflict with terms and/or definitions incorporated by reference.

As used herein, the terms "comprises," "comprising," or any other variation thereof are intended to cover a non-exclusive inclusion, such that a process, method, composition, article, or apparatus that comprises a list of elements does not include only those elements, but may include other elements not expressly listed or inherent to such process, method, composition, article, or apparatus. The term "exemplary" is used in the sense of "example" rather than "ideal."

As used herein, the singular forms "a," "an," and "the" include plural reference unless the context dictates otherwise. The terms "approximately" and "about" refer to being nearly the same as a referenced number or value. As used herein, the terms "approximately" and "about" should be understood to encompass ±5% of a specified amount or value.

Embodiments of the present disclosure include materials and related methods of preparing hemostatic agents or compositions thereof. The hemostatic agents herein may comprise one or more compounds, including one or more biomaterials that are biocompatible and/or derived from biological materials.

The hemostatic agents herein may comprise particles, e.g., with a controlled size and/or shape. The particles may be prepared by a customized (modified) electrospraying process with parameters selected to obtain particles with the desired characteristics. Electrospraying generally refers to a technique that generates a fine liquid aerosol into droplets through electrostatic charging. In the modified electrospraying process of the present disclosure, an electric field forces the liquid (e.g., chitosan salt solution) out of a needle, breaking the stream of the liquid to form individual droplets. Thus, for example, aspects of the present disclosure do not generate an aerosol in the manner of prior electrospraying processes. Once the particles are formed by electrospraying, they may be dried for immediate or future use. The parameters used in electrospraying and/or method of drying may provide for particles with a controlled size and/or shape as compared to particles prepared by other methods. For example, the hemostatic agents herein may comprise particles that are substantially spherical with a relatively narrow size distribution.

The compositions herein may comprise natural materials, e.g., natural polymers, capable of acting as hemostatic agents to reduce, stop, and/or prevent bleeding of tissue. While some particulate materials may act as good mechanical barriers and coagulants, their particle size and shape may negatively impact the delivery of such compounds and compositions thereof. For example, compounds with a relatively large particle size and/or fragmented particle shape may clog medical devices, making it difficult to deliver the hemostatic agent to a target site.

Without being bound by theory, it is believed that electrospraying and selecting the desired parameters of the modified electrospraying process of the present disclosure, and/or further processing the particles after electrospraying, may produce particles with desired characteristics, e.g., particle size, bulk density, and/or shape, to facilitate delivery to a target site for effective hemostatic treatment.

The compositions herein may comprise one or more materials that serve as hemostatic agent(s). The hemostatic agent(s) may be natural or derived from natural materials. In at least one example, the hemostatic agent(s) may be charged, e.g., cationic. For example, the hemostatic agent(s) may comprise one or more polysaccharides, such as chitosan and/or derivatives thereof, including but not limited to thiolated chitosan, PEGylated chitosan, catechol-modified chitosan, and carboxymethylchitosan; starch (e.g., potato or other plant starch); cellulose; alginate; or combinations thereof. In some examples herein, the hemostatic agent(s) comprise chitosan or derivative thereof, optionally in combination with one or more other hemostatic agents.

Chitosan is a linear polysaccharide formed of glucosamine units derived from chitin, the structural component of crustacean exoskeletons:

Chitosan is typically prepared by deacetylation of chitin with an alkaline reagent such as sodium hydroxide, yielding a water-soluble material. Chitosan is antimicrobial and cationic with natural bioadhesive properties that allow it to bind to negatively charged surfaces such as mucosal membranes and concentrate blood components, e.g., red blood cells, to promote coagulation. The hemostatic compositions herein may comprise chitosan. For example, the compositions may comprise chitosan with a crosslinking agent (e.g., the particles of the composition comprising crosslinked chitosan) and/or chitosan in the form of a biocompatible salt. Exemplary crosslinking agents for chitosan include, for example, tripolyphosphate (TPP), such as sodium TPP. Without being bound by theory, it is believed that chitosan and TPP crosslink via an ionic interaction, wherein positively-charged amine groups (e.g., protonated amine groups) of the chitosan interact with negatively-charged phosphate groups of the TPP to form a cross-linked structure. Exemplary chitosan salts of the compositions herein and/or that may be prepared and used in the electrospraying processes herein include, but are not limited to, chitosan acetate, chitosan lactate, chitosan succinate, chitosan glutamate, chitosan glycolate, and chitosan citrate.

The particles of the hemostatic agents herein may be prepared to have a desired particle size to facilitate administration to an internal bleeding site, e.g., via a catheter or other suitable medical device for endoscopic delivery. As discussed below, the preparation methods herein may provide for particles with a relatively narrow size distribution to promote controlled flow of the particles through a suitable fluid medium (e.g., a liquid such as water, saline solution or other aqueous solution; or a gas such as air, nitrogen, or oxygen).

Particle characteristics including size parameters may be characterized by morphological analysis, e.g., by imaging such as using optical microscopy. Statistical analysis for a plurality of particles may be provided by static automated imaging using an optical microscope. For example, a Malvern Morphologi 4 instrument may be used to employ static automated imaging to analyze various particle parameters by optical microscopy. Such particle characteristics that may be determined by optical microscopy include circle equivalent (CE) diameter, length, width, perimeter, area, maximum distance, sphere equivalent (SE) volume, and aspect ratio. Characteristics for a plurality of particles including average values and particle distribution data may be calculated from the individual values of the particles (e.g., average CE diameter, average maximum distance, average aspect ratio, etc.).

As used herein, and only for the purposes of this disclosure, the terms "average particle diameter" and "average diameter" refer to the average CE diameter of a plurality of particles, wherein CE diameter is defined as the diameter of a circle with the same area as the particle. According to some examples herein, the particles of the hemostatic agent(s) may have an average particle diameter ranging from about 100 μm to about 1 mm, such as about 100 μm to about 750 μm, about 150 μm to about 500 μm, about 250 μm to about 900 μm, about 200 μm to about 450 μm, about 250 μm to about 500 μm, about 250 μm to about 450 μm, about 250 μm to about 400 μm, about 300 μm to about 500 μm, about 300 μm to about 450 μm, about 550 μm to about 750 μm, or about 350 μm to about 450 μm. In some examples herein, the average particle diameter may be about 250 μm±60 μm, about 300 μm±60 μm, about 350 μm±60 μm, or about 450 μm±60 μm. Further, for example, the particles herein may have a maximum distance ranging from about from about 100 μm to about 1.2 mm, such as about 150 μm to about 1 mm, about 200 μm to about 550 μm, about 275 μm to about 950 μm, about 250 μm to about 500 μm, about 275 μm to about 550 μm, about 300 μm to about 700 μm, about 350 μm to about 550 μm, about 500 μm to about 700 μm, or 400 μm to about 650 μm. The term "maximum distance" of a particle as used in the present disclosure refers to the maximum distance among the set of all linear distances between any two points of the perimeter of a particle. According to some aspects of the present disclosure, the average of the maximum distances of a plurality of particles may range from about 400 μm to about 800 μm, for example from about 450 μm to about 700 μm, from about 500 μm to about 650 μm. For avoidance of confusion, each individual particle of a plurality of particles has a CE diameter and a maximum distance, wherein the "average particle diameter" or "average diameter" for the plurality of particles refers to the average of the CE diameters of the particles, and the "average of the maximum distance" for the plurality of particles refers to the average of the maximum distances of the particles.

In at least one example, the plurality of particles has an average diameter (average CE diameter) ranging from about 400 μm to about 600 μm, wherein the average of the maximum distances of the particles ranges from about 500 μm to about 700 μm. In at least one example, the plurality of particles has an average diameter (average CE diameter) ranging from about 450 μm to about 550 μm, wherein the average of the maximum distances of the particles ranges from about 500 μm to about 650 μm.

The $d_{50}$ alue is the particle CE diameter at which 50% of the particles have a smaller CE diameter (corresponding to the median particle diameter of the particle size distribution). Similarly, the $d_{10}$ value is the particle CE diameter at which 10% of the particles have a smaller CE diameter, the $d_{30}$ value is the particle CE diameter at which 30% of the particles have a smaller CE diameter, the $d_{70}$ value is the particle CE diameter at which 70% of the particles have a smaller CE diameter, and the $d_{90}$ value is the particle CE diameter at which 90% of the particles have a smaller CE diameter. According to some examples herein, the plurality of particles have a $d_{50}$ value ranging from about 450 μm to about 850 μm, such as about 500 μm to about 750 μm, or about 600 μm to about 700 μm; and/or a $d_{10}$ value ranging from about 300 μm to about 600 μm, such as about 400 μm to about 550 μm, or about 450 μm to about 500 μm; and/or a $d_{90}$ value ranging from about 500 μm to about 1 mm, such as about 650 μm to about 950 μm, or about 800 μm to about 900 μm.

Information on the range of particle sizes may be obtained from the steepness of a particle size distribution, which is defined as the ratio $d_{30}/d_{70} \times 100$. This ratio may be calculated from the $d_{30}$ and $d_{70}$ values of the particle size distribution. A higher steepness value indicates less deviation from the average particle size. The particles herein may have a relatively high steepness value indicative of a relatively narrow size distribution, e.g., a steepness value ranging from about 30 to about 90, such as from about 50 to about 80, from about 60 to about 90, from about 70 to about 90, from about 80 to about 90, from about 75 to about 85, or from about 60 to about 80.

The aspect ratio (ρ) of a particle provides information about its shape, wherein the aspect ratio in two dimensions is defined as the length along the particle's width divided by the length, which may be determined based on the major axis and the minor axis of the particle. The major axis is the axis passing through the center of mass of the particle at an orientation corresponding to the minimum rotational energy of the shape. The minor axis is the axis passing through the center of mass of the particle at a right angle to the major axis. To determine the length of a particle, lines from all points on the perimeter of the particle are projected onto the major axis (the projected lines being parallel to each other and perpendicular to the major axis). The longest distance between the points where two of these line projections meet the major axis is the length. Similarly, to determine the width of a particle, lines from all points on the perimeter of the particle are projected onto the minor axis (the projected lines being parallel to each other and perpendicular to the minor axis). The longest distance between the points where two of these line projections meet the minor axis is the width. Aspect ratios approaching 1 indicate more uniform, rounded particles, wherein any cross-section of a sphere has an aspect ratio of 1. The aspect ratio of a particle may be determined by imaging (e.g., optical microscopy) and software capable of determining the minor axis, major axis, width, and length of each particle. The average aspect ratio for a plurality of particles may be determined by averaging the aspect ratios of the particles, such as by static automated imaging.

The particles herein may have a rounded, spherical shape to facilitate flow through a fluid medium in a delivery device. In some examples, the particles may have an average aspect ratio greater than 0.6, greater than 0.7, or greater than 0.8, e.g., ranging from about 0.6 to 1.0, from about 0.7 to 1.0, or from about 0.8 to 1.0. For instance, the average aspect ratio may range from about 0.7 to about 0.98, from about 0.8 to about 0.95, or from about 0.85 to about 0.95. For purposes of this disclosure, the term "substantially spherical" means a rounded three-dimensional shape having the general shape of a sphere. For example, any cross-sectional dimension through the center point of a particle that is substantially spherical varies by less than 10% as compared to any other cross-sectional dimension through the center point of the particle. Phrased another way, the longest cross-sectional dimension of a substantially spherical particle varies less than 10% as compared to the shortest cross-sectional dimension.

In at least one example, the plurality of particles has an average diameter (average CE diameter) ranging from about 400 µm to about 600 µm, wherein the average of the maximum distance ranges from about 500 µm to about 700 µm and/or the average aspect ratio ranges from about 0.7 to about 0.9. In at least one example, the plurality of particles has an average diameter (average CE diameter) ranging from about 450 µm to about 550 µm, wherein the average of the maximum distance ranges from about 500 µm to about 650 µm and/or the average aspect ratio ranges from about 0.7 to about 0.9. In these examples, the particles may be substantially spherical in shape.

In at least one example, the plurality of particles has an average diameter (average CE diameter) ranging from about 400 µm to about 600 µm, and an average aspect ratio ranging from about 0.7 to about 0.9 and/or a steepness value ranging from about 60 to about 90. In at least one example, the plurality of particles has an average diameter (average CE diameter) ranging from about 400 µm to about 600 µm, and an average aspect ratio ranging from about 0.7 to about 0.9 and/or a steepness value ranging from about 70 to about 80. In at least one example, the plurality of particles has an average diameter (average CE diameter) ranging from about 450 µm to about 550 µm, and an average aspect ratio ranging from about 0.7 to about 0.9 and/or a steepness value ranging from about 70 to about 80. In these examples, the particles may be substantially spherical in shape.

The particles herein also may have a bulk density suitable for facilitating delivery to a target site. A lower bulk density generally represents more fluffy particles, which may be desirable for effective delivery. A bulk density that is too low may result in static that impedes delivery, however. Accordingly, the particles herein may have a relatively low bulk density, without being too low so as to cause static, in order to facilitate delivery to a target site. In some examples, the bulk density of the particles may be less than 0.7 g/L, for example ranging from about 0.05 g/mL to about 0.7 g/L, from about 0.08 g/mL to about 0.126 g/mL, from about 0.1 g/mL to about 0.7 g/L, from about 0.2 g/mL to about 0.7 g/mL, from about 0.05 g/mL to about 0.6 g/mL, from about 0.2 g/mL to about 0.5 g/mL, from about 0.05 g/mL to about 0.5 g/mL, from about 0.3 g/mL to about 0.6 g/mL, from about 0.3 g/mL to about 0.5 g/mL, from about 0.05 g/mL to about 0.4 g/mL, from about 0.05 g/mL to about 0.3 g/mL, from about 0.05 g/mL to about 0.2 g/mL, from about 0.1 g/mL to about 0.2 g/mL, or from about 0.2 g/mL to about 0.3 g/mL. Bulk density may be measured by filling a known volume with the particles and weighing the powder (without compressing the material) to calculate the bulk density in g/mL.

Figure 1:
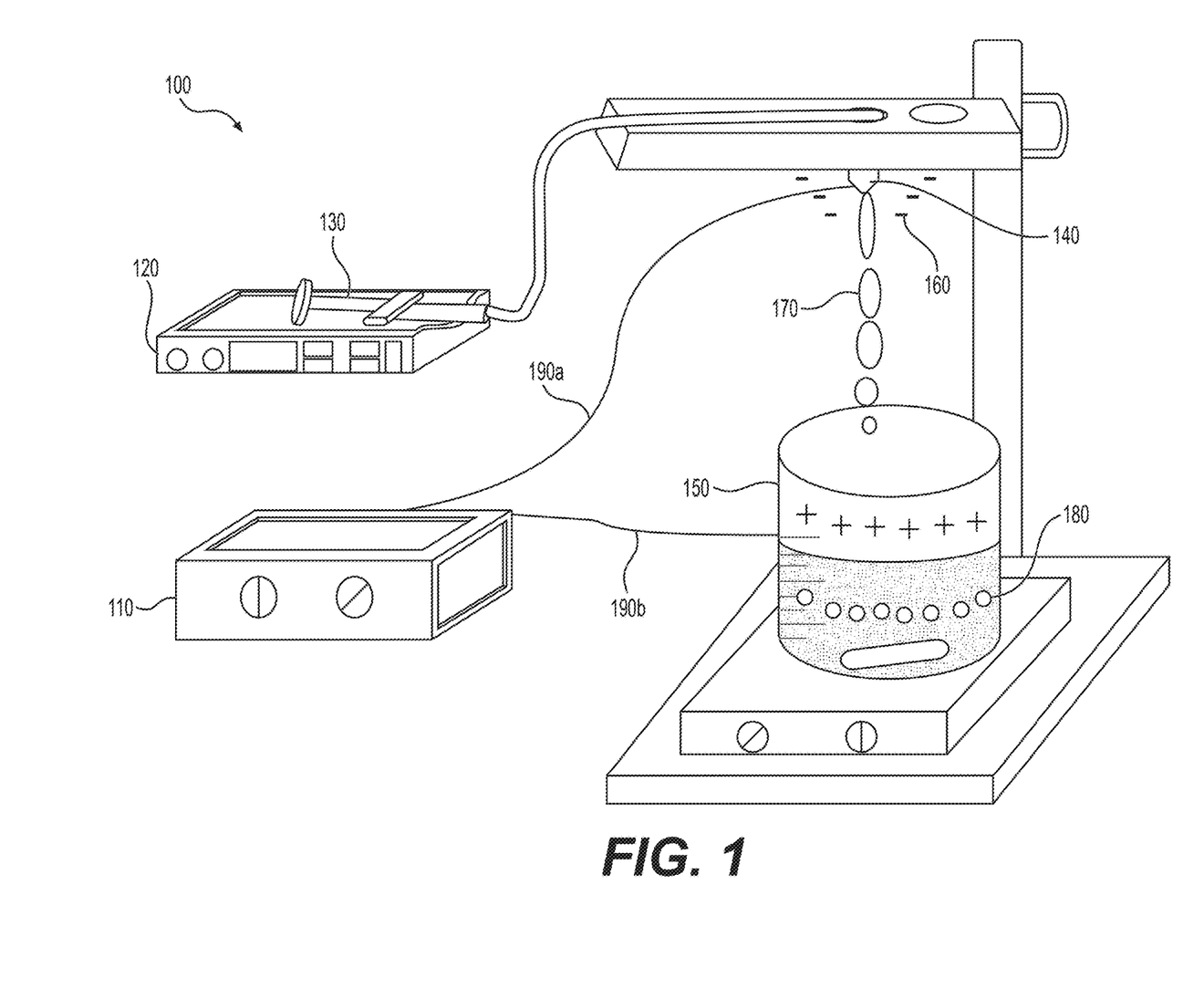
FIG. 1 illustrates an exemplary schematic of an electrospray system, in accordance with some aspects of the present disclosure.

Exemplary methods of preparing the particles herein will be described below with reference to FIG. 1. Methods of preparing the particles herein may include preparing a solution, electrospraying the solution to produce particles, washing the resulting particles, and/or drying the particles. It is understood that one or more of these steps may be omitted. For example, the method may include preparing a solution, electrospraying the solution to produce particles, and drying the resulting particles (e.g., optionally washing the particles); or electrospraying a solution to produce particles, and washing and/or drying the resulting particles.

Preparing the solution may include combining a hemostatic agent, e.g., chitosan, with a suitable acid, e.g., one or more organic acids such as acetic acid, lactic acid, succinic acid, glutamic acid, glycolic acid, citric acid, or a combination thereof. In at least one example, preparing the solution comprises combining chitosan with citric acid and/or acetic acid. In some examples, the solution may comprise up to 10% by weight chitosan relative to the total weight or volume of the solution, e.g., from about 0.5% to about 10.0% by weight chitosan or from about 0.5% to about 3.0% by weight chitosan relative to the total weight or volume of the solution. For example, the solution may comprise from about 0.5% to about 7.5%, from about 1.0% to about 6.0%, from about 2.5% to about 5.5%, from about 3.0% to about 6.5%, from about 5.5% to about 9.5%, from about 4.5% to about 7.0%, from about 0.5% to about 2.5%, from about 1.0% to about 2.0%, from about 1.0% to about 3.0%, from about 2.0% to about 3.0%, or from about 2.5% to about 4.5% by weight chitosan, relative to the total weight or volume of the solution. In some examples, the solution may comprise up to about 5% by weight of the organic acid(s), e.g., from about 0.5% to about 5.0% by weight, or from about 1.0% to about 2.5% by weight, relative to the total weight of chitosan. For example, the solution may comprise from about 0.5% to about 7.0%, from about 1.0% to about 5.0%, from about 0.5% to about 3.0%, or from about 1.0% to about 2.0% by weight organic acid (e.g., citric acid and/or acetic acid), relative to the total weight of the chitosan. The organic acid(s) may be present as an aqueous solution, e.g., citric acid solution, acetic acid solution, etc. In at least one example, the chitosan is combined with a solution comprising citric acid, acetic acid, and water (e.g., citric acid added to an aqueous acetic acid solution). The chitosan/organic acid solution (or other chitosan salt solution according to the present disclosure) may have a viscosity at 25° C. less than 10,000 cPs, for example, less than 8,000 cPs, less than 5,000 cPs, less than 3,500 cPs, less than 3,200 cPs, less than 3,000 cPs, less than 2,800 cPs, less than 2,500 cPs, less than 2,200 cPs, less than 2,000 cPs, less than 1,800 cPs, or less than 1,500 cPs, e.g., a viscosity at 25° C. ranging from about 1,000 cPs to about 10,000 cPs, from about 1,500 cPs to about 8,000 cPs, from about 1,500 cPs to about 7,500 cPs, from about 2,000 cPs to about 5,000 cPs, from about 3,000 cPs to about 7,000 cPs, from about 1,000 cPs to about 4,000 cPs, from about 2,500 cPs to about 5,500 cPs, from about 1,000 cPs to about 3,200 cPs, from about 1,200 cPs to about 1,500 cPs, from about 1,200 cPs, to about 2,000 cPs, from about 1,400 cPs to about 1,800 cPs, from about 1,500 cPs to about 3,000 cPs, from about 1,500 cPs to about 2,500 cPs, or from about 2,000 cPs to about 2,500 cPs. Viscosity may be measured with a viscometer. For example, viscosity at 25° C. may be measured with a viscometer employing a circulating water temperature of 25° C., a speed of 50 RPM (revolutions per minute), testing a 12 mL sample with a total testing time of 8 minutes, wherein the viscosity is reported as the average of the viscosity measured for the last 3 minutes of the total testing time. An exemplary instrument for measuring viscosity is a Brookfield Viscometer DV2T Extra. Higher viscosities may be expected to increase the amount of time to prepare the particles. In at least some cases, and depending on the viscosity, higher viscosities may provide greater difficulty in achieving a consistent, uniform flow during electrospraying. Further, in some cases, the viscosity may decrease over time, e.g., facilitating electrospraying.

The chitosan/organic acid solution (or other chitosan salt solution according to the present disclosure) may then be passed through an electrospraying system. FIG. 1 illustrates an exemplary electrospraying system, wherein syringe 130 containing the solution is connected to pump 120 (e.g., optionally part of an automatic injection system). Pump 120 may be, for example, a mechanical pump or a peristaltic pump. Once pump 120 is turned on, the solution is passed from syringe 130 to the electrospraying instrument, e.g., through a connecting supply tube, such that the solution exits through needle 140 of the instrument, needle 140 serving as a nozzle. While FIG. 1 illustrates one syringe 130 and one electrospray needle 140, the system may include two or more syringes and/or two or more electrospray needles (e.g., each syringe coupled to a corresponding needle, two or more syringes coupled to a single needle, one syringe coupled to two or more needles in parallel or series, etc.) to increase the throughput of droplets and volume of particles produced. The throughput of droplets may also be increased by replacing the syringe with a pressure pot and pumping the solution (e.g., with a mechanical or peristaltic pump) through the electrospraying instrument using a pressurized system.

The needle 140 is charged, such that the solution when exiting the needle 140, passes through an electric field towards collection unit 150. The electric field is created by the applied voltage from power source 110 and the distance of needle 140 from collection unit 150. Electrode 190a connects power source 110 to needle 140, and electrode 190b connects power source 110 to collection unit 150. The solution also may be charged, e.g., having a positive charge due to a positive charge of the hemostatic agent in the solution. As the solution flows through needle 140 serving as a nozzle, the solution disperses into individual, charged droplets. According to some examples herein, the amount of voltage may provide for the formation of unstable droplets. For example, the charged droplets may assume a generally conical shaped area 160, in a manner somewhat similar to a Taylor cone but without forming a stable Taylor cone as characterized in prior electrospraying processes. Thus, for example, the electric field may guide the unstable droplets towards the collection unit 150 and break surface tension of the liquid on the needle 140. At the tip of area 160, the droplets (e.g., unstable droplets) form a fine jet spray. This jet spray likewise becomes unstable and breaks up into a mist of fine droplets, represented as a plume 170. The droplets repel each other and move towards a grounded medium provided by the collection unit 150. The particles thus produced are received by collection unit 150.

As mentioned above, the parameters of the modified electrospraying process herein may be selected to produce particles of the desired size and shape. To alter particle size distribution, for example, the applied voltage may be increased to speed up the flow of the solution (the drop rate of the solution) through the tip of needle 140. This affects the stability of the droplets (e.g., in view of the lack of a stable Taylor cone), which as a result, alters the size of the droplets. A bead of the solution may form at the tip of needle 140 and drop when the surface tension can no longer hold the bead in place. The electric field may at least partially drive the sizes of the droplets as they leave needle 140 to form particles collected in collection unit 150. Exemplary voltages according to the present disclosure may range from about 10 kV to about 30 kV, or from about 9 kV to about 25 kV. The voltage may be selected to be below a threshold at which damage to the hemostatic agent is expected to occur. In the case of chitosan, for example, the polysaccharide structure is expected to break down at temperatures greater than about 50° C. Accordingly, voltages less than 25 kV may be used to avoid damaging the chitosan in the solution.

Other aspects of the electrospraying system herein may be selected to produce particles having the desired characteristics, e.g., size and/or shape. For example, e.g., the size of the electrospraying needle and the distance from the tip of the needle (i.e., nozzle) to the grounded medium (collection unit). In some examples, the needle may have a gauge size ranging from 16 to 23 or from 16 to 22, e.g., a needle gauge of 16, 18, 20, 21, 22, or 23. Different gauge sizes may alter the droplet size. For example, a larger gauge size may produce larger droplets and hence larger particles, and a smaller gauge size may produce smaller droplets and hence smaller particles. Further, for example, the distance from the electrospraying needle tip to the collection unit may range from about 5 cm to about 15 cm.

According to some aspects of the present disclosure, a voltage ranging from about 10 kV to about 30 kV and a needle gauge of 23 mm, or a voltage ranging from about 15 kV to about 23 kV and a needle gauge of 22 mm, may be used to produce particles having an average diameter ranging from about 200 μm to about 800 μm.

The grounded medium may comprise a suitable liquid for receiving the particles. In the case of water-soluble natural polymers such as chitosan, for example, an aqueous solution may be used. Volatile solvents such as alcohols may be less suitable since water-soluble polymers are less likely to remain distributed throughout the medium and may aggregate together. In some examples, collection unit 150 may include an aqueous solution comprising an ionic crosslinker (crosslinking agent), e.g., a reversible ionic crosslinker (crosslinking agent). Exemplary crosslinkers (also referred to herein as crosslinking agents) suitable for the methods herein include, but are not limited to, tripolyphosphate (TPP) such as sodium tripolyphosphate, ethanol, and sodium hydroxide. In some examples, the crosslinker (crosslinking agent), e.g., TPP, may be present in the solution in an amount ranging from about 1% by weight to about 15% weight, such as from about 3% by weight to about 15% by weight, such as from about 5% by weight to about 10% by weight, or about 5% by weight to about 7% by weight, relative to the total weight or volume of the solution. Without being bound by theory, it is believed that the crosslinker (crosslinking agent) generates a spherical complex around the particle droplets as they enter the aqueous solution of the collection unit 150. For example, the complex, e.g., TPP complex, may help to prevent particles from aggregating or otherwise sticking together. Further, the crosslinker (crosslinking agent) may crosslink functional groups (e.g., amine groups) of the chitosan as mentioned above. Thus, for example, TPP as a crosslinker (crosslinking agent) may crosslink with amine groups (e.g., protonated amine groups) of the chitosan to produce chitosan-TPP crosslinked particles. Accordingly, the crosslinker (crosslinking agent) may assist in particle formation while avoiding aggregation, such that the particles maintain a porous structure, their rounded shapes, and relatively uniform sizes.

Once the electrospraying is complete, or once a desired amount of particles has been collected in collection unit 150, the particles may be separated from the solution via any appropriate technique, e.g., via filtration, a funnel, etc. The particles optionally may be rinsed or washed to remove residual crosslinker (crosslinking agent) solution and excess crosslinker (crosslinking agent) complex surrounding the particles. For example, the particles may be rinsed or washed with water (e.g., deionized water), an alcohol such as ethanol or isopropyl alcohol, or mixtures thereof. The particles may be rinsed/washed once or any number of times sufficient to remove residual crosslinker (crosslinking agent). In some examples, the particles are not rinsed or washed. According to some aspects of the present disclosure, the rinsed/washed particles may be placed onto a sieve and spread into a single, thin layer, so as to separate out the particles from one another. The particles optionally may further be rinsed/washed with water (e.g., deionized water), an alcohol (e.g., ethanol, isopropyl alcohol, or other alcohols), or mixtures thereof.

The methods herein include drying the particles, e.g., to further maintain the desired size and shape of particles. Because the aqueous solutions used for the modified electrospraying process herein and the grounded medium are less volatile than some other liquids such as alcohols, the rinsed/washed particles may include residual water. This moisture may cause the particles to aggregate to form larger, irregularly-shaped particles that are more difficult to deliver to a target site during a medical procedure.

Accordingly, the particles may undergo at least one drying process. Different drying processes may affect the shape, size, and/or porosity of the particles. In the methods herein, the drying process(es) may include freezing, exposure to reduced pressure (e.g., vacuum pressure), gentle heating, or a combination thereof. According to some aspects to the present disclosure, the particles are freeze dried. For example, the particles may be cooled until frozen and then placed in a vacuum chamber to allow the solid ice crystals to sublimate. Sublimation may avoid substantial aggregate observed when the particles include liquid water. See Example 2 below. As discussed above, excess water present on the particles may result in relatively large, agglomerated, and irregularly-shaped particles. Sublimation of water present in the particles may reduce agglomeration and misshaping of the particles.

In some examples, the particles may be frozen to or at a temperature ranging from about −5° C. to about −30° C., such as from about −10° C. to about −20° C., wherein the temperature may be slowly lowered from room temperature (about 22° C.) to the target temperature over the span of several minutes to hours. According to some examples herein, the particles may be dried using a dynamic freeze-drying system, e.g., using a rotating drum apparatus. For example, the particles may be frozen and maintained at freezing temperatures (e.g., about −55° C.) while an inner drum rotates. An outer drum also may cycle through elevated temperatures (−20° C.) to promote uniform drying of the particles as they rotate around the dryer. The dynamic freeze-drying system may be operated at reduced pressure.

Once frozen and/or as part of the freezing process, the particles may be placed in a vacuum chamber for sublimation. For example, the vacuum chamber may be maintained at a pressure less than 150 Pa (1.13 mm Hg), such as a pressure ranging from about 5 Pa to about 150 Pa (0.038-1.13 mm Hg) or from about 50 Pa to about 150 Pa (0.38-1.13 mm Hg), e.g., a pressure of about 5 Pa, about 10 Pa, about 50 Pa, about 75 Pa, or about 100 Pa. According to some aspects of the present disclosure, the pressure within the vacuum chamber may be reduced from atmospheric pressure over the course of several minutes to several hours, e.g., over a period of time ranging from about 10 minutes to about 4 hours, from about 30 minutes to about 3 hours, from about 1 hour to about 2 hours. The duration of time within the vacuum chamber may range from a couple of hours to a couple of days. For example, the particles may be placed in the vacuum chamber for a duration ranging from about 30 minutes about 4 days, such as from 1 hour to about 48 hours, from about 1 hour to about 24 hours, from about 1.5 hours to about 12 hours, from about 1 hour to about 4 hours, from about 2 hours to about 10 hours, from about 4 hours to about 8 hours, from about 6 hours to about 12 hours, from about 12 hours to about 18 hours, from about 12 hours to about 24 hours, or from about 24 hours to about 48 hours. Optionally, the vacuum chamber may be gently heated.

The particles produced according to the present disclosure may be porous. For example, the particles may have a porosity greater than 80%, such as ranging from about 85% to about 95%, or from about 87% to about 97%. Porosity may be measured via mercury intrusion porosimetry with a pressure of about 60,000 psia. An exemplary mercury intrusion porosimeter suitable for measuring the porosity of the particles herein is an AutoPore V by Micromeritics®, which can measure pore diameters from 3 nm to 1100 μm. Different factors of the manufacturing process may be adjusted to achieve the desired porosity value, including the concentration of chitosan in the chitosan salt solution, the concentration of TPP in the collection bath, and the amount of freezing time. For example, lower concentrations of chitosan and TPP are expected to result in lower crosslinking density and more porous particles. Further, for example, longer freezing times are expected to promote retention of particle structure without aggregation or collapse of pore structure during the drying process. Different temperature ramping techniques can be implemented to provide different pore structures in the resulting particle.

While the modified electrospraying and drying processes described above may be used to prepare substantially spherical particles of a desired size, the particles optionally may undergo one or more further processing steps. In some examples, the dried particles may be milled or ground to further reduce the size of the particles. The particles may be milled or ground by any appropriate methods or devices, e.g., a pestle or grinder.

EXAMPLES

The following examples are intended to illustrate the present disclosure without, however, being limiting in nature. It is understood that the present disclosure encompasses additional aspects and embodiments consistent with the foregoing description and following examples.

Example 1

Chitosan acetate is blended using 2% solids of chitosan (by weight based on the volume of the solution), 1% of citric acid (by weight based on the weight of chitosan) in a 1% acetic acid/water solution (by weight based on the volume of the solution). The blended chitosan is then passed through a 22 gauge needle and through an electric field generated by an applied voltage of 20-25 kV in a modified electrospraying process as described herein. The particles fall into a collection bath made up of water and 7% sodium tripolyphosphate (TPP). Once a selected volume of chitosan is electrosprayed, the particles are decanted from the collection bath and washed multiple times with deionized water to remove excess solution (salt and uncrosslinked TPP). The cleaned particles are placed on a sieve in a monolayer, cleaned again with deionized water through a squirt bottle and then cleaned with isopropyl alcohol. The alcohol displaces water out of the particles and removes salt crystals. The sieve is then placed in a freezer (e.g., at a temperature ranging from −80° C. to −20° C.). Once frozen, the particles are placed in a vacuum chamber to sublime water off at a slow rate. The resulting chitosan-TPP crosslinked particles have an average diameter of 300-500 μm with a bulk density of around 0.3-0.7 g/mL and an average aspect ratio greater than 0.6.

Example 2

Three different batches of chitosan particles prepared according to the modified electrospraying method of Example 1 were dried according to different methods to determine the effect on particle size and shape.

Figure 2:
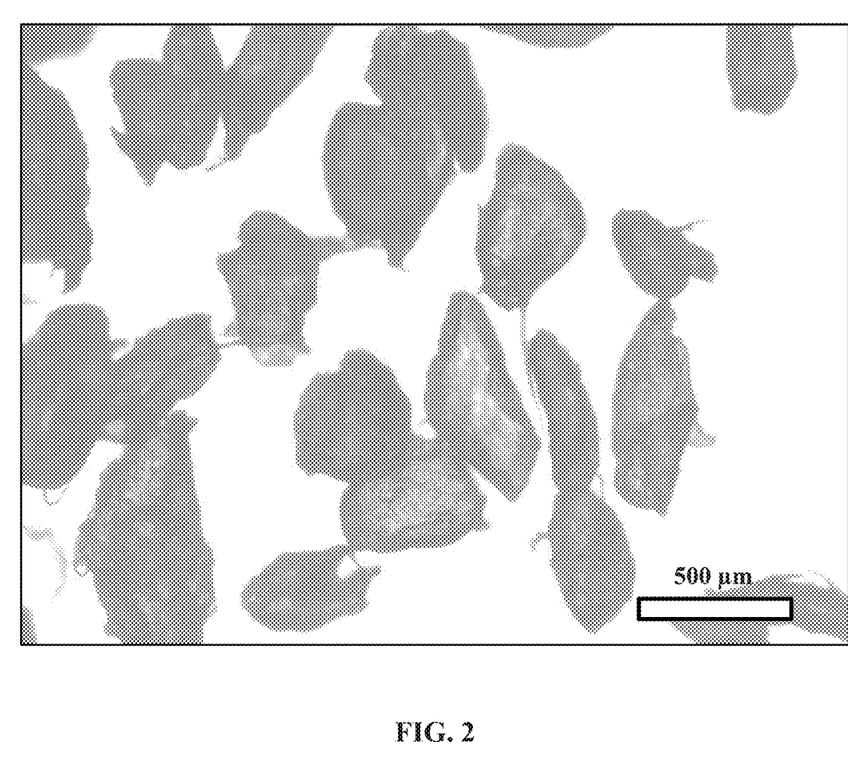
FIGS. 2-4 show images of chitosan particles that have undergone different drying processes, as discussed in Example 2.

A first batch of chitosan particles was allowed to air dry in open air. The particles had a CE diameter in the range of about 100 μm to about 900 μm. As shown in FIG. 2, the dried particles appeared as oblong shards. The size bar in FIG. 2 is 500 μm.

Figure 3:
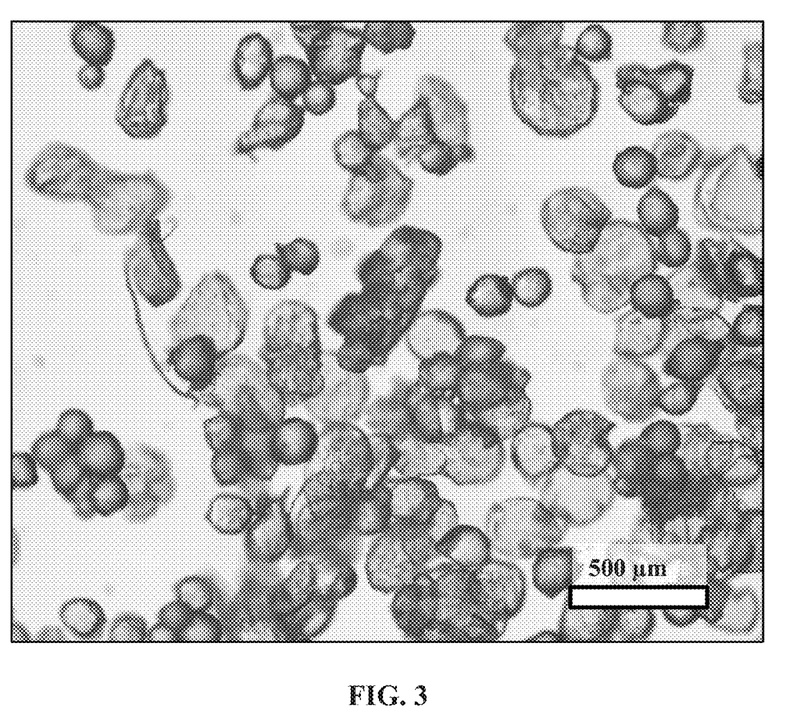

A second batch of chitosan particles was placed in a vacuum chamber for about 96 hours to dry. The particles had an average diameter ranging from about 200 μm to about 400 μm and a bulk density of about 0.7 g/mL. As shown in FIG. 3, the particles were more spherical but somewhat aggregated. The size bar in FIG. 3 is 500 μm.

Figure 4:
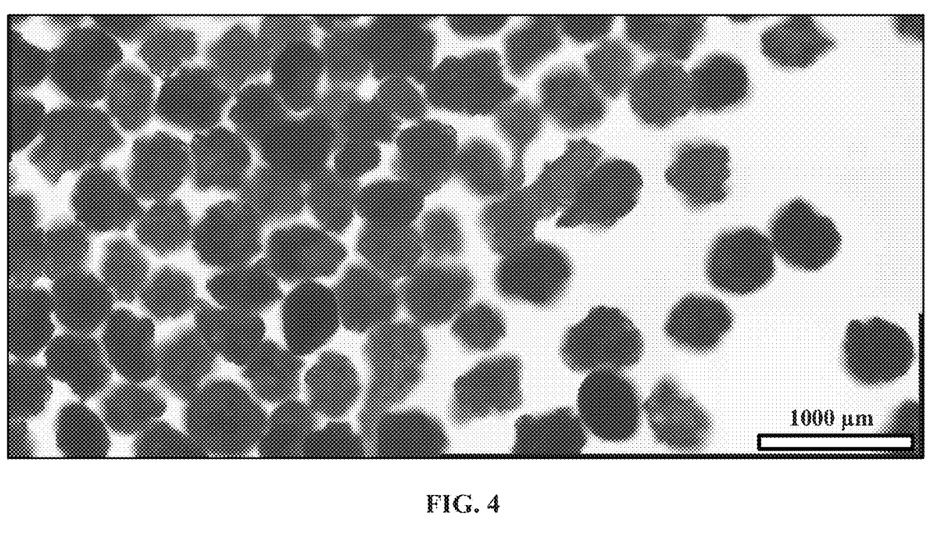

A third batch of chitosan particles was frozen at a temperature of about −20° C. and then placed in a vacuum chamber and allowed to evacuate to a pressure of 0.7 mm Hg over the course of 2-5 hours. The temperature was then maintained at 35° C. for 2 hours to allow the particles to dry via sublimation. The particles had an average diameter ranging from about 200 μm to about 425 μm and a bulk density of about 0.2 g/mL to about 0.3 g/mL. As shown in FIG. 4, the particles were more spherical and separated as compared to the particles shown in FIG. 3. The size bar in FIG. 4 is 1000 μm.

Example 3

Figure 5:
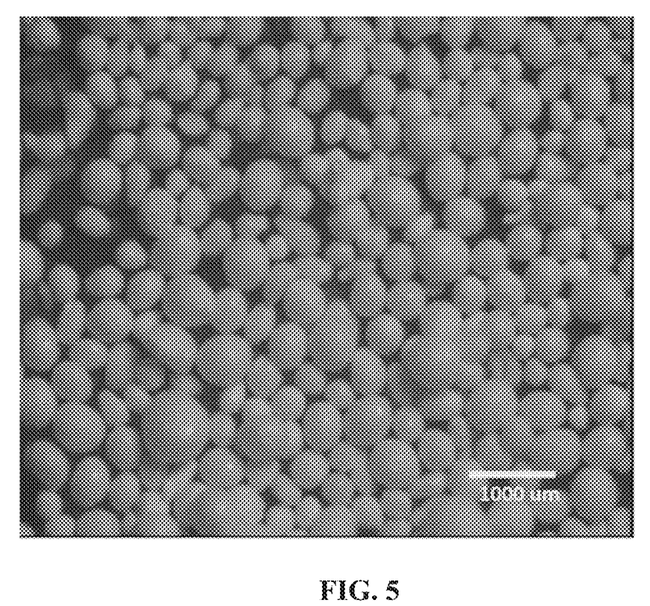
FIGS. 5 and 6 show images of chitosan particles according to some aspects of the present disclosure, as discussed in Example 3.
Figure 6:
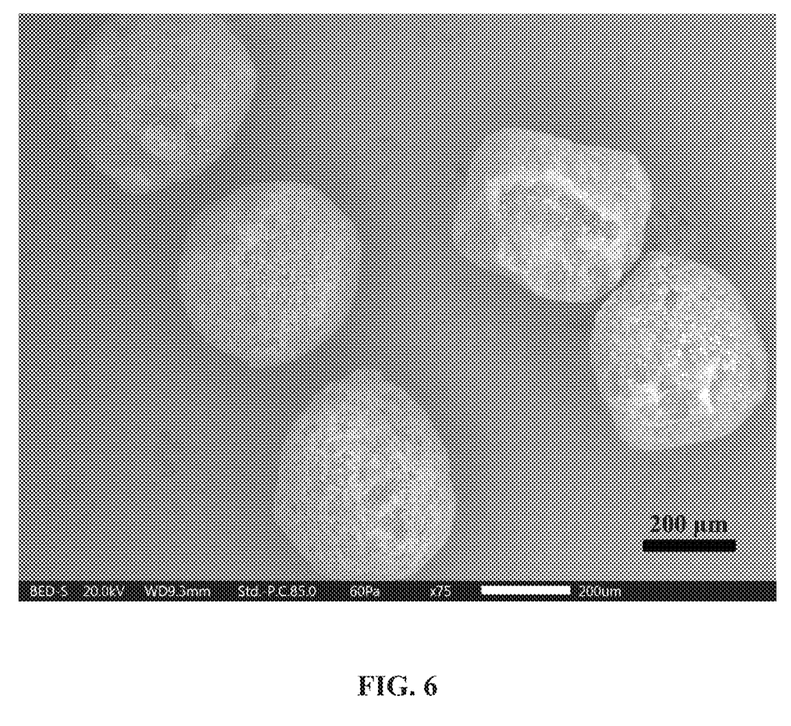

Chitosan particles were prepared according to the modified electrospraying method of Example 1. In this example, the particles were dried using a dynamic freeze-drying system where the particles were frozen and maintained at freezing temperatures of about −55° C. while the inner drum rotated. The outer drum also cycled through elevated temperatures of about −20° C. to uniformly dry the particles as they rotated around the dryer. The resulting material was a highly porous, more uniform and homogenous population of particle morphology and density. The particles are shown in FIG. 5 (light microscopy) and FIG. 6 (scanning electron microscopy). The size bar in FIG. 5 is 1000 μm, and the size bar in FIG. 6 is 200 μm.

Aspects of the present disclosure include the following numbered exemplary embodiments:

1. A composition comprising a plurality of particles of chitosan such as chitosan with a crosslinking agent and/or a chitosan salt, wherein the plurality of particles have: an average diameter ranging from about 150 μm to about 500 μm, such as from about 300 μm to about 450 μm, optionally wherein the plurality of particles have a steepness value ranging from about 30 to about 90 such as from about 50 to about 80, or from about 60 to about 80; and an average aspect ratio greater than 0.6, greater than 0.7, or greater than 0.8, the plurality of particles being substantially spherical in shape.
2. The composition of embodiment 1, wherein a bulk density of the plurality of particles ranges from about 0.2 g/mL to about 0.7 g/mL, such as from about 0.3 g/mL to about 0.5 g/mL.
3. The composition of embodiment 1 or 2, wherein the chitosan salt is chitosan acetate, chitosan lactate, chitosan succinate, chitosan glutamate, chitosan glycolate, or chitosan citrate.
4. The composition of any one of the preceding embodiments, wherein the composition further comprises a liquid.
5. A method of preparing the composition of any one of the preceding embodiments, wherein the method comprises electrospraying a chitosan salt solution through a needle.
6. The method of embodiment 5, wherein the chitosan salt solution has a viscosity ranging from about 1,500 cPs to about 3,000 cPs.
7. The method of embodiment 5 or 6, wherein the chitosan salt solution comprises from about 0.5% to about 10% by weight chitosan.
8. The method of any one of embodiments 5-7, wherein the electrospraying includes applying a voltage of about 9 kV to about 25 kV to the needle.
9. The method of any one of embodiments 5-8, wherein the needle is a 21 gauge needle or a 22 gauge needle.
10. The method of any one of embodiments 5-9, wherein the chitosan salt solution is electrosprayed into an aqueous solution comprising a crosslinking agent such as sodium tripolyphosphate.
11. The method of any one of embodiments 5-10, wherein the method further comprises freeze drying the plurality of particles.
12. The method of embodiment 11, wherein the freeze drying is performed for a period of time ranging from 30 minutes to 48 hours, such as from 2 hours to 12 hours, or 4 hours to 6 hours.

13. The method of any one of embodiments 5-12, wherein the method further comprises rinsing the plurality of particles with a liquid after electrospraying and/or before freeze drying.
14. The method of embodiment 13, wherein the liquid comprises water, an alcohol, or a mixture thereof.
15. Use of the composition of any one of embodiments 1-4 as a hemostatic agent.
16. A method of preparing a composition, the method comprising: electrospraying a chitosan salt solution through a needle to produce a plurality of particles of chitosan such as chitosan with a crosslinking agent and/or the chitosan salt; and freeze drying the plurality of particles; wherein the plurality of particles have an average diameter ranging from about 150 μm to about 500 μm and an average aspect ratio greater than 0.6, the plurality of particles being substantially spherical in shape.
17. The method of embodiment 16, wherein the chitosan salt comprises chitosan acetate, chitosan lactate, chitosan succinate, chitosan glutamate, chitosan glycolate, or chitosan citrate.
18. The method of embodiment 16, wherein the average diameter of the plurality of particles ranges from about 300 μm to about 450 μm.
19. The method of embodiment 16, wherein the average aspect ratio of the plurality of particles is greater than 0.8.
20. The method of embodiment 16, wherein the plurality of particles has a steepness value ranging from about 50 to about 80.
21. The method of embodiment 16, wherein the chitosan salt solution is electrosprayed into an aqueous solution comprising the crosslinking agent.
22. The method of embodiment 21, wherein the crosslinking agent comprises sodium tripolyphosphate.
23. A method of preparing a composition, the method comprising: electrospraying a chitosan salt solution through a needle to produce a plurality of particles of chitosan such as chitosan with a crosslinking agent and/or the chitosan salt; and freeze drying the plurality of particles; wherein the plurality of particles have an average diameter ranging from about 300 μm to about 500 μm, an average aspect ratio greater than 0.6, the plurality of particles being substantially spherical in shape, and a bulk density ranging from about 0.2 g/mL to about 0.7 g/mL.
24. The method of embodiment 23, wherein the chitosan salt solution comprises from about 0.5% to about 10% by weight chitosan.
25. The method of embodiment 23, wherein the chitosan salt solution has a viscosity ranging from about 1,500 cPs to about 3,000 cPs.
26. The method of embodiment 23, wherein the electrospraying includes applying a voltage of about 9 kV to about 25 kV to the needle.
27. The method of embodiment 23, wherein the needle is a 21 gauge needle or a 22 gauge needle.
28. The method of embodiment 23, wherein the freeze drying is performed for a period of time ranging from 30 minutes to 48 hours.
29. The method of embodiment 23, wherein the method further comprises rinsing the plurality of particles with a liquid after electrospraying and before freeze drying.
30. The method of embodiment 29, wherein the liquid comprises water, an alcohol, or a mixture thereof.
31. A composition comprising a plurality of particles of chitosan such as chitosan with a crosslinking agent and/or a chitosan salt, wherein the plurality of particles have: an average diameter ranging from about 250 μm to about 500 μm; an average aspect ratio greater than 0.6, the plurality of particles being substantially spherical in shape; and an average bulk density ranging from about 0.2 g/mL to about 0.7 g/mL.
32. The composition of embodiment 31, wherein the chitosan salt comprises chitosan acetate, chitosan lactate, chitosan succinate, chitosan glutamate, chitosan glycolate, or chitosan citrate.
33. The composition of embodiment 31, wherein the composition is in the form of a powder.
34. The composition of embodiment 31, wherein the plurality of particles has a steepness value ranging from about 50 to about 80.
35. The composition of embodiment 31, wherein the bulk density ranges from about 0.3 m/mL to about 0.5 g/mL.

Other aspects of the present disclosure will be apparent to those skilled in the art from consideration of the specification and practice of the examples disclosed herein. It is intended that the specification and examples be considered as exemplary only, with a true scope and spirit of the present disclosure being indicated by the following claims.

What is claimed is:
1. A method of preparing a composition, the method comprising:
   electrospraying a solution consisting essentially of a chitosan salt through a needle into an aqueous solution comprising a crosslinking agent to produce a plurality of particles comprising chitosan and the crosslinking agent; and
   freeze drying the plurality of particles;
   wherein the solution has a viscosity at 25° C. ranging from about 1,500 cPs to about 8,000 cPs; wherein the crosslinking agent comprises tripolyphosphate; wherein the plurality of particles have an average diameter ranging from about 100 μm to about 750 μm and an average aspect ratio ranging from about 0.6 to 1.0; and wherein the plurality of particles has a porosity greater than 80%, as measured by mercury intrusion porosimetry.
2. The method of claim 1, wherein the chitosan salt is chitosan acetate, chitosan lactate, chitosan succinate, chitosan glutamate, chitosan glycolate, or chitosan citrate.
3. The method of claim 1, wherein the average diameter of the plurality of particles ranges from about 400 μm to about 600 μm.
4. The method of claim 1, wherein the average aspect ratio of the plurality of particles ranges from about 0.8 to 1.0.
5. The method of claim 1, wherein the plurality of particles has a steepness value ranging from about 30 to about 90.
6. The method of claim 1, wherein the plurality of particles are substantially spherical in shape.
7. The method of claim 1, wherein the plurality of particles have an average diameter ranging from about 300 μm to about 750 μm and a bulk density ranging from about 0.1 g/mL to about 0.7 g/mL.
8. The method of claim 1, wherein the electrospraying includes applying a voltage of about 10 kV to about 30 KV to the needle.
9. The method of claim 1, wherein the needle is a 23 gauge needle.

10. The method of claim 1, wherein the solution comprises from about 0.5% to about 10% by weight chitosan, based on a volume of the solution.

11. A method of preparing a composition, the method comprising:
   electrospraying a solution comprising a chitosan salt through a needle into an aqueous solution comprising a crosslinking agent to produce a plurality of particles consisting essentially of chitosan and the crosslinking agent; and
   freeze drying the plurality of particles;
   wherein the solution has a viscosity at 25° C. ranging from about 1,500 cPs to about 8,000 cPs; wherein the crosslinking agent comprises tripolyphosphate; wherein the plurality of particles have an average diameter ranging from about 300 μm to about 750 μm, an average aspect ratio ranging from about 0.6 to 1.0, and a bulk density ranging from about 0.1 g/ml to about 0.7 g/ml; and wherein the plurality of particles has a porosity greater than 80%, as measured by mercury intrusion porosimetry.

12. The method of claim 11, wherein the composition is in the form of a powder.

* * * * *